United States Patent
El-Faham et al.

(10) Patent No.: US 9,636,747 B1
(45) Date of Patent: May 2, 2017

(54) FUNCTIONALIZED SILICA FOR THE SYNTHESIS OF METAL NANOPARTICLES

(71) Applicant: KING SAUD UNIVERSITY, Riyadh (SA)

(72) Inventors: Ayman Sadek Ahmed El-Faham, Riyadh (SA); Moustafa Mohamed Gaballa El-Sayed Fouda, Riyadh (SA); Zeid Abdullah Mohammad Al Othman, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 5 days.

(21) Appl. No.: 15/145,781

(22) Filed: May 3, 2016

(51) Int. Cl.
  *B22F 9/24* (2006.01)
  *C07F 7/02* (2006.01)
  *C22B 3/00* (2006.01)

(52) U.S. Cl.
  CPC .............. *B22F 9/24* (2013.01); *C07F 7/025* (2013.01); *C22B 11/04* (2013.01); *B22F 2301/255* (2013.01); *B22F 2304/054* (2013.01)

(58) Field of Classification Search
  CPC  B22F 9/24; B22F 2301/255; B22F 2304/054; C07F 7/025; C22B 11/04
  See application file for complete search history.

(56) References Cited

U.S. PATENT DOCUMENTS

| | | |
|---|---|---|
| 8,480,784 B2 | 7/2013 | Malekzadeh et al. |
| 2010/0317819 A1 | 12/2010 | De Keyzer et al. |
| 2015/0343421 A1* | 12/2015 | Boday ................ B01J 20/28019 428/402 |

* cited by examiner

*Primary Examiner* — Melvin C Mayes
*Assistant Examiner* — Michael Forrest
(74) *Attorney, Agent, or Firm* — Richard C. Litman

(57) ABSTRACT

The functionalized silica for the synthesis of metal nanoparticles includes a silica surface functionalized by a hydrazino-triazine derivative. A method of preparing the functionalized silica includes the steps of combining silica gel and a triazine derivative in a first organic solvent to form a mixture; heating the mixture for about two hours; isolating a white solid by filtration; washing the solid with the first organic solvent; suspending the white solid in a second organic solvent to form a suspension; adding hydrazine hydrate to the suspension while stirring; heating the suspension for about 3 hours to form the silica surface functionalized by a hydrazino-triazine derivative; and isolating the silica surface functionalized by a hydrazino-triazine derivative by filtration.

12 Claims, 10 Drawing Sheets

FUNCTIONALIZED SILICA FOR THE SYNTHESIS OF METAL NANOPARTICLES

BACKGROUND OF THE INVENTION

1. Field of the Invention

The present invention relates to nanotechnology, and particularly to functionalized silica for the synthesis of metal nanoparticles.

2. Description of the Related Art

In recent years, nanotechnology has gained enormous scientific progress in the field of research and technology. Nanotechnology is usually used for studying and application of nanoparticles, which can be used in different fields, such as physics, chemistry, biology, and material science, and other promising fields. Currently, there are almost two thousand nanotechnology-based consumer products according to an analysis by Nanotechproject.com. Among all the nano-products, almost 25% products are impregnated with nano-sized silver.

Silver nanoparticles (AgNPs) are used in a wide range of applications, including pharmaceuticals, cosmetics, medical devices, food ware, clothing and water purification, among other uses, due to their antimicrobial properties. A variety of preparation routes have been reported for the preparation of silver nanoparticles. Notable examples include biological methods, photoreduction, and reduction of silver salts by different chemical reductants, such as ascorbic acid, sodium citrate, hydrazine, sodium borohydride, or some solvents, including EtOH and DMF. For protection of silver nanoparticles by silica gel, various methods are reported, including photoreduction and ultrasound.

Among all the synthetic methods, chemical reduction is most commonly used. However, toxic compounds, such as borohydride, are usually involved. Studies have focused on the green synthetic approaches to avoid using hazardous materials. Environmentally benign monosaccharides and polysaccharides are used to reduce the Ag $(NH_3)^{2+}$ complexes formed by reacting $AgNO_3$ with ammonia to AgNPs. Previous studies have produced AgNPs with sizes ranging from 50-200 nm and silver hydrosols ranging from 20-50 nm. However, aggregation during synthesis can hinder the production of AgNPs with small and uniform sizes. The control of their size, shape, dispersity, and in particular, the combination of metal nanoparticles with a specific heterogeneous support, is essential to prevent aggregation and/or coalescence, to obtain enhanced activity and selectivity in a desired application. Recently, some researches have reported the synthesis of silver nanoparticles immobilized on silica gel, which provides good solid support for adsorption due to its chemical, thermal, and mechanical stability.

Thus, silica support functionalized with triazine-hydrazino derivatives for preparing metal nanoparticles thereby solving the aforementioned problems are desired.

SUMMARY OF THE INVENTION

The functionalized silica for the synthesis of metal nanoparticles includes a silica surface functionalized by a hydrazino-triazine derivative, having the structural formula:

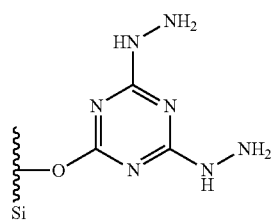

or the formula:

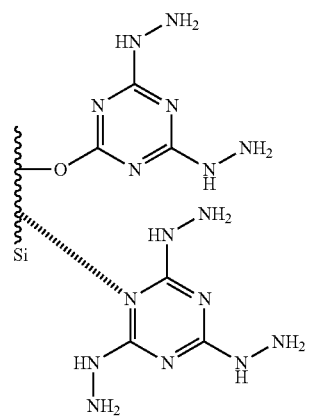

wherein Si is silica ($SiO_2$).

Another example of a silica surface functionalized by a hydrazino-triazine derivative is represented by the following structural formula:

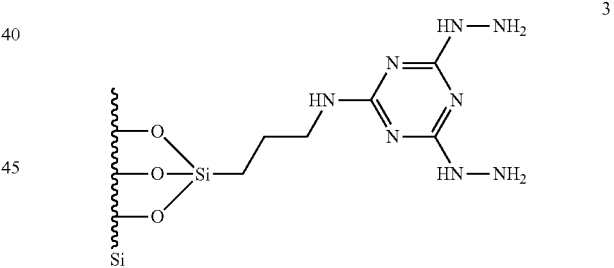

A method of preparing a silica surface functionalized by a hydrazino-triazine derivative represented by the structures 1 or 2 above comprises the steps of combining silica gel and a triazine derivative in a first organic solvent to form a mixture; heating the mixture for about two hours; isolating a white solid by filtration; washing the solid with the first organic solvent; suspending the white solid in a second organic solvent to form a suspension; adding hydrazine hydrate to the suspension while stirring; heating the suspension for about 3 hours to form the silica surface functionalized by a hydrazino-triazine derivative; and isolating the silica surface functionalized by a hydrazino-triazine derivative by filtration.

The method of preparing a silica surface functionalized by a hydrazino-triazine derivative of represented by structure 3 comprises the steps of reacting silica gel and 3-aminopropyltrimethoxysilane under reflux conditions for about eight hours in a first organic solvent to form silica-supported aminopropyltrimethoxysilane; isolating the silica-supported aminopropyltrimethoxysilane by filtration; washing the silica-supported aminopropyltrimethoxysilane with a first organic solvent; drying the silica-supported aminopropyltrimethoxysilane product at about 0.110° C.; reacting the silica-supported aminopropyltrimethoxysilane with cyanuric chloride and diisopropylethylamine in a second organic solvent at room temperature under stirring for about 12 hours to form silica-functionalized aminopropyltrimethoxysilane-diisopropylethylamine derivative; isolating the silica-functionalized aminopropyltrimethoxysilane-diisopropylethylamine derivative; washing the silica-functionalized aminopropyltrimethoxysilane-diisopropylethylamine derivative with a mixture of organic solvents; drying the silica-functionalized aminopropyltrimethoxysilane-diisopropylethylamine derivative; reacting the silica-functionalized aminopropyltrimethoxysilane-diisopropylethylamine derivative with hydrazine hydrate under reflux conditions for about 4 hours to form the silica surface-functionalized hydrazino-triazine derivative; and isolating the silica surface-functionalized hydrazino-triazine derivative by filtration.

A method of preparing metal nanoparticles comprises combining an aqueous solution of a metal salt with a silica surface functionalized by a hydrazino-triazine derivative under stirring at room temperature for about 12 hours to form metal nanoparticles immobilized on the silica surface and isolating the metal nanoparticles by centrifugation.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
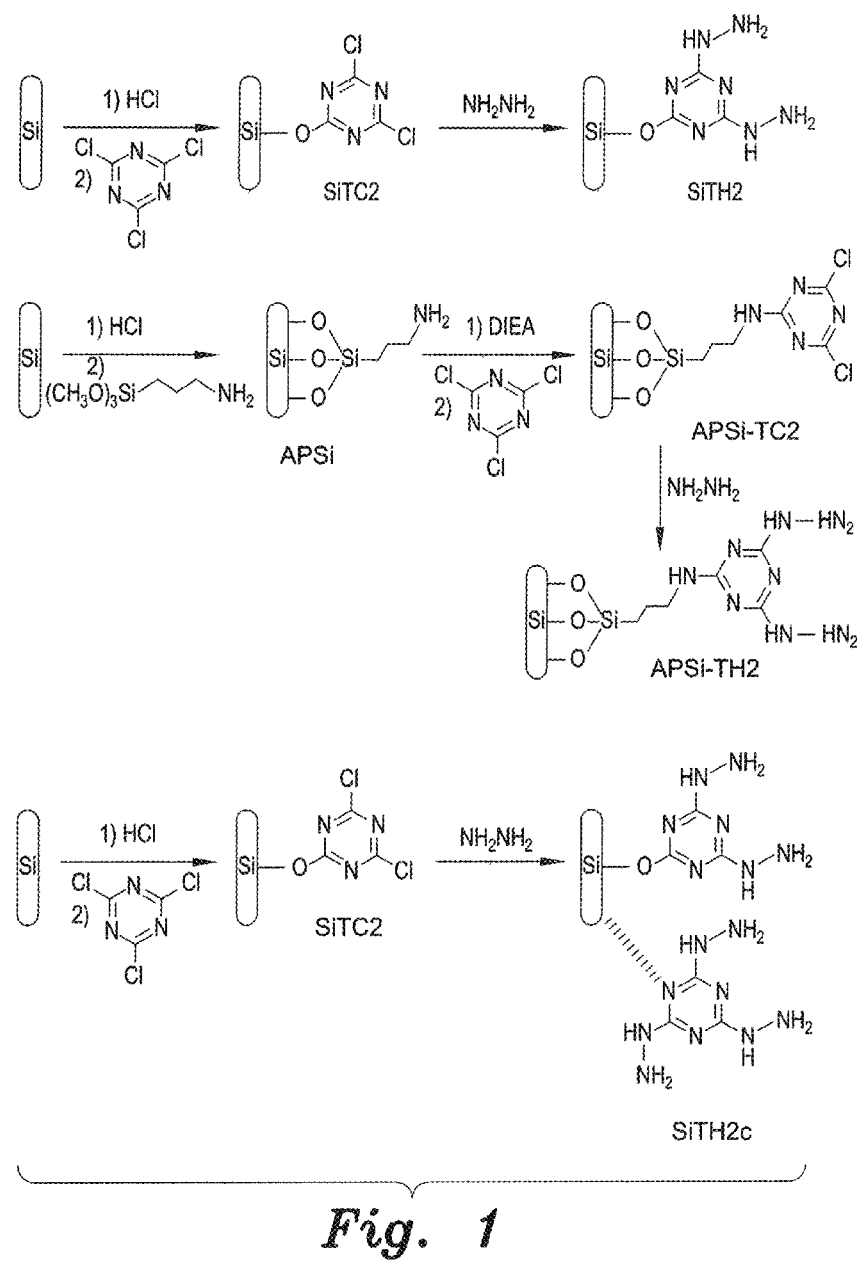
FIG. 1 shows three reaction schemes for preparing functionalized silica for the synthesis of metal nanoparticles according to the present invention.

The disclosure falls into three general categories: (1) Chemical modification of silica surface with hydrazino-triazine derivatives; (2) Application of the silica surface functionalized with hydrazino-triazine derivatives in the synthesis of different metal nanoparticles in aqueous/non aqueous media; and (3) Application in the synthesis of different metal nanoparticles in solvent free condition solid/solid phase synthesis.

The method of preparing functionalized silica for the synthesis of metal nanoparticles represented by the structures 1 or 2 above comprises the steps of combining silica gel and a triazine derivative in a first organic solvent to form a mixture; heating the mixture for about two hours; isolating a white solid by filtration; washing the solid with the first organic solvent; suspending the white solid in a second organic solvent to form a suspension; adding hydrazine hydrate to the suspension while stirring; heating the suspension for about 3 hours to form the silica surface functionalized by a hydrazino-triazine derivative; and isolating the silica surface functionalized by a hydrazino-triazine derivative by filtration to obtain:

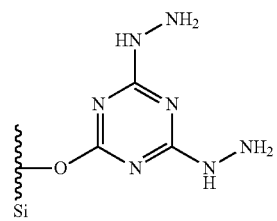

or

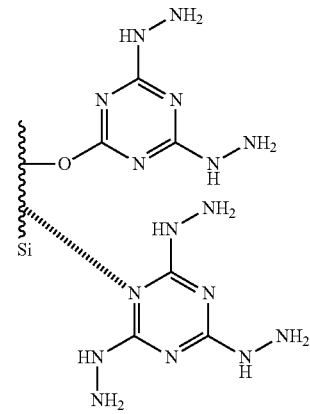

The silica gel can include activated silica gel, wherein the silica gel is activated by refluxing the silica gel with concentrated hydrochloric acid for about 24 hours; washing the silica gel with water until free of chloride; and drying the silica gel at about 100° C. for about 24 hours. The first organic solvent can include dichloromethane and the second organic solvent can include acetonitrile. The method can further include heating the isolated surface functionalized by a hydrazino-triazine derivative in an oven at 100° C. for about 12 hours.

Another method of preparing a silica surface functionalized by a hydrazino-triazine derivative represented by structure 3 below comprises the steps of: reacting silica gel and 3-aminopropyltrimethoxysilane under reflux conditions for about eight hours in a first organic solvent to form silica-supported aminopropyltrimethoxysilane; isolating the silica-supported aminopropyltrimethoxysilane by filtration; washing the silica-supported aminopropyltrimethoxysilane with a first organic solvent; drying the silica-supported aminopropyltrimethoxysilane product at about 110° C.; reacting the silica-supported aminopropyltrimethoxysilane with cyanuric chloride and diisopropylethylamine in a second organic solvent at room temperature under stirring for about 12 hours to form a silica-functionalized aminopropyltrimethoxysilane-diisopropylethylamine derivative; isolating the silica-functionalized aminopropyltrimethoxysilane-diisopropylethylamine derivative; washing the silica-functionalized aminopropyltrimethoxysilane-diisopropylethylamine derivative with a mixture of organic solvents; drying the silica-functionalized aminopropyltrimethoxysilane-diisopropylethylamine derivative; reacting the silica-functionalized aminopropyltrimethoxysilane-diisopropylethylamine derivative with hydrazine hydrate under reflux conditions for about 4 hours to form the silica surface-functionalized hydrazino-triazine derivative; and isolating the silica surface-functionalized hydrazino-triazine derivative by filtration.

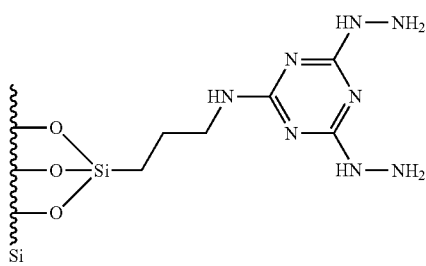

3

The method can further comprise washing the silica surface-functionalized hydrazino-triazine derivative (3) with hot ethanol, ether and methanol. The silica gel can be activated silica gel prepared by refluxing the silica gel with concentrated hydrochloric acid for about 48 hours; washing with water until free of chloride and drying at about 100° C. for about 24 hours to obtain the activated silica gel. Typically, the first organic solvent is toluene and the second organic solvent is tetrahydrofuran, and the mixture of organic solvent comprises tetrahydrofuran, dichloromethane and methanol.

The method of preparing metal nanoparticles comprises combining an aqueous solution of a metal salt with a methanolic mixture of silica surface functionalized by a hydrazino-triazine derivative represented by the structural formula 1, 2, or 3 above to form a reaction mixture; stirring the reaction mixture at room temperature for about 12 hours to form metal nanoparticles immobilized on the silica surface; and isolating the metal nanoparticles by centrifugation. The method can further comprise washing the metal nanoparticles with methanol and drying the nanoparticles under vacuum. The metal salt is silver nitrate and the metal nanoparticles are silver nanoparticles. Additionally, different metal salts (such as $AgNO_3$, $CuX_2$, $Ni(X)_2$, $Co(X)_2$, Au salt, $PdCl_2$, where (X=Cl or $NO_3$), can be reacted with the modified silica 1, 2, or 3 in ecofriendly solvent, such as water or methanol, to generate the metal nanoparticles.

The method can further comprise the step of sonicating the reaction mixture for about an hour. The method of preparing metal nanoparticles according can further comprise the step of heating the reaction mixture at 80° C. for 1 minute. Additionally, the method of heating can be conducted by microwave irradiation at a power of 600 Watts for about 5 seconds to attain a temperature of about 60° C.

As used herein, the term "Nanoparticle" refers to a particle having at least one dimension sized between 1 and 100 nanometers. The metal nanoparticles can include gold or silver nanoparticles. In some embodiments, the nanoparticles disclosed herein are from about 5 nm to about 500 nm in diameter.

In order to perform the synthesis of the silica functionalized with the hydrazino-triazine derivative the following chemicals were used: silica gel 60 (0.032-0.063 mm, Merck Darmstadt Co.) with high surface area of 60-540 $m^2/g$, 3-aminopropyltrimethoxy silane (Sigma-Aldrich) and $CuCl_2$, $NiCl_2$, $CoCl_2$ and silver nitrate salts were also purchased from Merck. 2, 4, 6-trichloro-1, 3, 5-triazine (TCT). All the chemicals used in the synthesis were analytical grade. The evaluation of crystal structure was achieved by X-ray diffractometer (XRD) (X'Pert PRO, PANalytical BV, Almelo, the Netherlands) using CuKα radiation. The studies of size, morphology, and composition of the NPs were performed by means of scanning electron microscope (SEM) and transmission electron microscopy (TEM), equipped with energy dispersive X-ray (EDX) analysis. Histograms of AgNPs' size distribution were calculated from the TEM images by measuring the diameters of at least 50 particles. Samples for TEM studies were prepared by placing drops of the AgNP solutions on carbon-coated TEM. The silica surface functionalized by a hydrazino-triazine derivative can be synthesized based on the reaction strategy, as illustrated in FIG. 1.

The present teachings will be understood more readily by reference to the following examples, which are provided by way of illustration Example 1

Synthesis of (SiTH2) (Structure 1)

Figure 2:
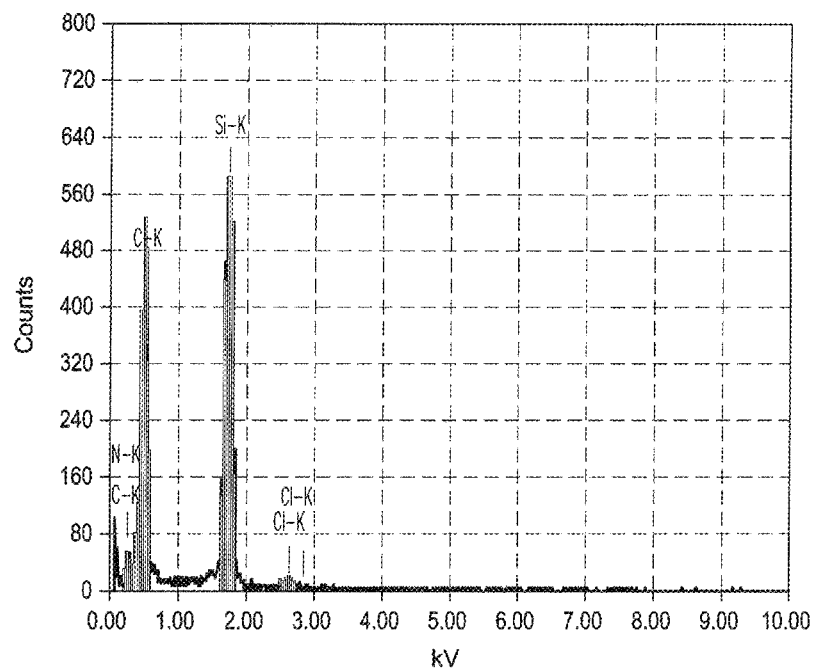
FIG. 2 shows the X-ray diffraction pattern of silica supported 2,4,6-trichloro-1,3,5-triazine (SiTC2).
Figure 3:
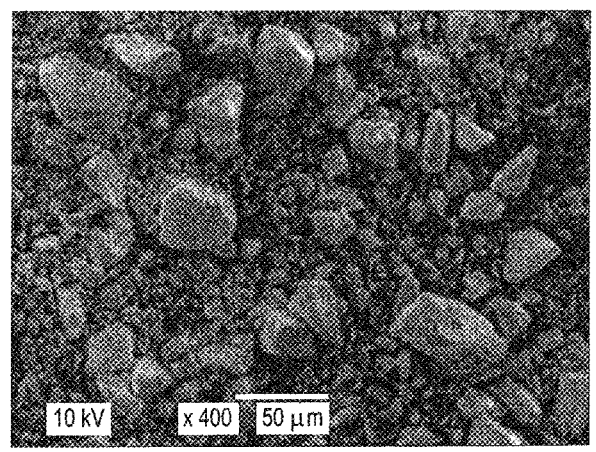
FIG. 3 shows the scanning electron micrograph (SEM) of silica supported 2,4,6-trichloro-1,3,5-triazine (SiTC2).

The desired silica supported 2, 4, 6-trichloro-1, 3, 5-triazine; (Silica-TCT) was prepared in our laboratory by simple approach. The mixture of silica 30 gm (Silica gel 60-540 mesh) and TCT (13.2 g) was mixed together and heated (2 h) in dichloromethane (200 mL), followed by filtration, washing with DCM, and drying in air to afford white solid (SiTC2); yield: 33.8 gm (Total loading is 0.688 mmol/gm). 30 gm of (SiTC2) was suspended in acetonitrile (200 mL), and 30 mL of hydrazine hydrate was added. The reaction mixture was stirred under heating for 3-4 h, filtered, washed with acetonitrile and ether, and dried in air, which yielded white slightly pink color (SiTH2); yield: 33.4 gm (Total loading is 0.663 mmol/gm). FIG. 2 shows the X-ray diffraction pattern of silica-supported 2,4,6-trichloro-1,3,5-triazine (SiTC2). FIG. 3 shows the scanning electron micrograph (SEM) of silica-supported 2,4,6-trichloro-1,3,5-triazine (SiTC2).

Example 2

2-Synthesis of (SiTH2c) (Structure 2)

Figure 4:
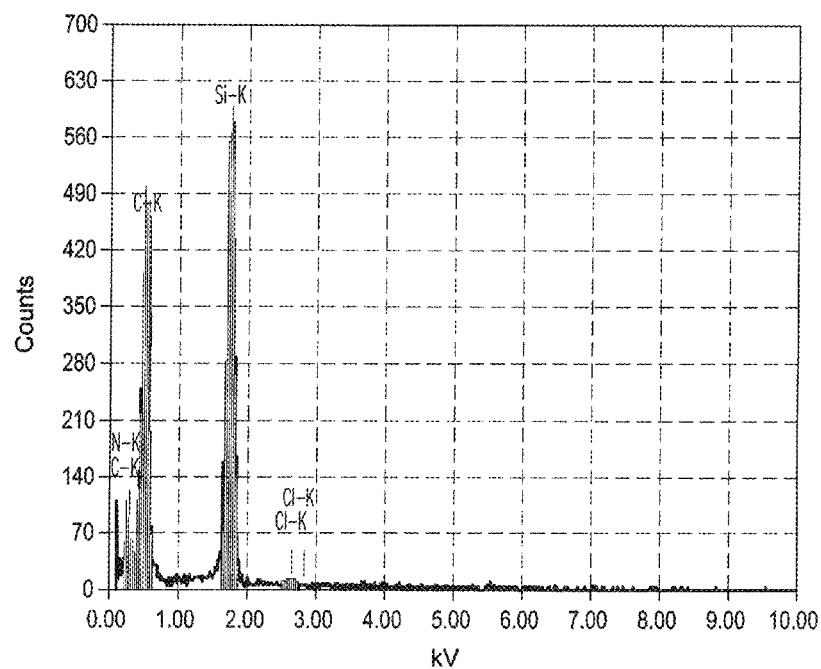
FIG. 4 shows the X-ray diffraction pattern of SiTH2.
Figure 5:
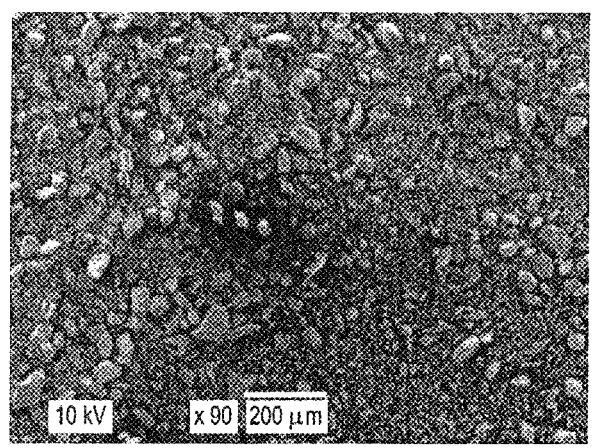
FIG. 5 shows the SEM of SiTH2

First, the desired silica-supported 2,4,6-trichloro-1,3,5-triazine (SiTC2c) was prepared in the laboratory by simple approach. The mixture of silica 16 gm (60-230 mesh Alpha Chimca) and TCT (3.68 gm, 20 mmol) was mixed together in dry dichloromethane (dry DCM, 200 mL), and the mixture was stirred at room temperature for 2 h. Then, after evaporation of the solvent, the mixture was suspended in acetonitrile (100 mL), and then hydrazine hydrate was added (12 mL). The reaction mixture was stirred at room temperature overnight and then heated for 2 h, filtration, wash with acetonitrile, ether, and then dried, gave a white solid (SiTH2c); yield:25.6 gm before drying. The product was dried in oven at 100° C. overnight. (Loading 3.508 mmol/gm) (From 25.6−16=9.6 gm). FIG. 4 shows the X-ray diffraction pattern of SiTH2 and FIG. 5 shows the SEM of SiTH2.

Example 3

Synthesis of Activated Silica; ASiTH2 (Structure 2)

About 50 gm of silica was activated by conc. HCl (500 mL). The mixture was refluxed for 24 h, filtered, washed with water until free of chloride, and dried at 100° C. for 24 h. About 20 gm of the activated silica and TCT (10 gm) were mixed together in dichloromethane (200 mL), the mixture was stirred under reflux for 3-4 h, followed by filtration, washed with DCM and dried in air, yielding 23.9 gm of white solid (ASiTC2), yield 0.195 gm/gm, (Loading 1.06 mmol TCT/gm). The activated silica ASiTC2 (20 gm) was suspended in acetonitrile (200 mL) and 40 mL of hydrazine hydrate was added. The reaction mixture was stirred under heating for 4 h, filtered, washed with acetonitrile, ether, and dried in air, gave off white slightly pink color; ASiTH2 (Loading 0.215/gm loading 1.168 mmol TCT/gm).

Example 4

Synthesis of APSiTH2 (Structure 3)

A 100 mL concentrated HCl solution was added to 100 g silica gel, and the mixture was refluxed for 48 h. It was filtered in vacuum and washed with distilled water to remove completely the HCl. The sample was dried in a vacuum oven for 24 h at 120° C. In a round-bottomed flask equipped with a condenser and a magnetic stirrer, a mixture of activated Si (1 g) and 3-aminopropyltrimethoxysilane (APTS) (3 mL) in 20 mL of anhydrous toluene was stirred under reflux conditions for 8 h. The reaction mixture was filtered, and the solid material was washed with toluene, THF, and dried in a vacuum oven at 110° C. to afford the product APSi. Next, about 1 g of APSi was added to a solution of cyanuric chloride (1.85 g, 10 mmol) and diisopropylethylamine (DIPEA) (10 mmol, 1.7 mL) in THF (10 mL). The reaction mixture was shaken overnight at room temperature. The solid material was separated by filtration, washed with hot THF, DCM, and methanol, and dried to afford APSiTC2. About 1 g of APSiTC2 was added to a solution of hydrazine hydrate 80% (5 mL) in ethanol (20 mL). The reaction mixture was refluxed for 4 h, cooled to room temperature, and the solid material was separated by filtration, washed with hot ethanol, ether, and methanol, and dried under vacuum to afford APSiTH2 [loading 1.98 mmol/gm.

Example 5

Synthesis of APFSiTH2 (Structure 3)

In a round-bottomed flask equipped with a condenser and a magnetic stirrer, a mixture of fumed silica (1 g, 770 nm) and concentrated HCl (10 mL, 8 M) was refluxed for 24 h. The mixture was filtered, and the white powder was washed with distilled water until all HCl was removed. The solid was dried under vacuum at 120° C. In a round-bottomed flask equipped with a condenser and a magnetic stirrer, a mixture of activated silica FS-380 (1 g) and 3-aminopropyltrimethoxysilane (3 mL) in 20 mL of anhydrous toluene was stirred under reflux conditions for 8 h. The reaction mixture was filtered, and the solid material was washed with toluene, THF, and dried in a vacuum oven at 110° C. to afford the product APFSi. Next, 1 g of APFSi was added to a solution of cyanuric chloride (1.85 g, 10 mmol) and diisopropylethylamine (DIPEA) (10 mmol, 1.7 mL) in THF (10 mL). The reaction mixture was shaken overnight at room temperature. The solid material was separated by filtration, washed with hot THF, DCM, and methanol, and dried to afford the product APFSiTC2. 1 g of APFSiTC2 was added to a solution of hydrazine hydrate 80% (5 mL) in ethanol (20 mL). The reaction mixture was refluxed for 4 h, cooled to room temperature and the solid material was separated by filtration, washed with hot ethanol, ether, methanol, and dried under vacuum to afford the final functionalized silica APFSiTH2 with loading 2.94 mmol/gm.

All the newly synthesized and functionalized silica was used for the preparation of metal nanoparticles (such as AgNPs) using different conditions: (a) solid-liquid in methanol-water medium at room temperature; (b) using ultrasonic irradiation; or (c) solid-solid using normal heating or microwave irradiation. All of them gave a very good result in very short time.

Example 6

Synthesis of Silver (Ag) Nanoparticles Using Solid-Liquid in Methanol-Water Medium A solution of 0.1 gm $AgNO_3$ in 50 mL of water was added to a suspended solution of 0.1 gm of the modified silica in 50 mL methanol under stirring at room temperature. The reaction mixture was stirred at room temperature overnight. The color changed from colorless to reddish black then to black. The AgNPs immobilized on silica were collected using centrifuge, washed with methanol, and then dried under vacuum.

Example 7

Synthesis of Silver (Ag) Nanoparticles Using Ultrasonic Irradiation

A solution of 0.1 gm AgNO3 in 50 mL of water was added to a suspended solution of 0.1 gm of the modified silica in 50 mL methanol under sonication at 30° C. The reaction mixture was sonicated at the same temperature for 1 h, then kept at room temperature overnight. The AgNPs immobilized on silica were collected using centrifuge, washed with methanol, and then dried under vacuum.

Example 8

Synthesis of Silver (Ag) Nanoparticles Using Solid-Solid Using Normal Heating or Microwave Irradiation A solution of about 0.1 gm of $AgNO_3$ was mixed well with 0.1 gm of the modified silica at room temperature. The solid mixture was heated at 80° C. for 1 min using normal heating conditions (microwave condition 600 Watts, 60° C. for 5 sec. The AgNPs immobilized on silica were suspended in methanol-water mixture 1:1, and then collected using centrifuge, washed with methanol, and then dried under vacuum.

Figure 6:
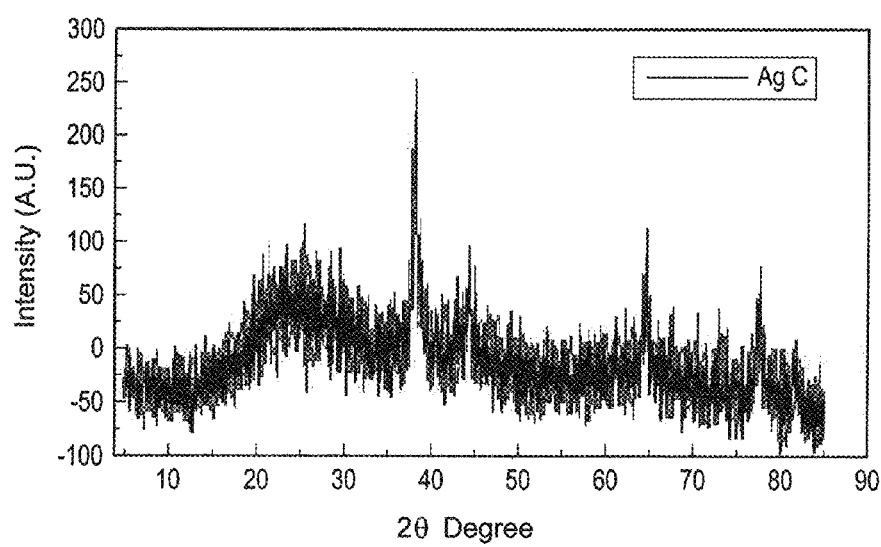
FIG. 6 is the X-ray diffraction pattern of SiTH2-silver nanoparticle solution
Figure 7A:
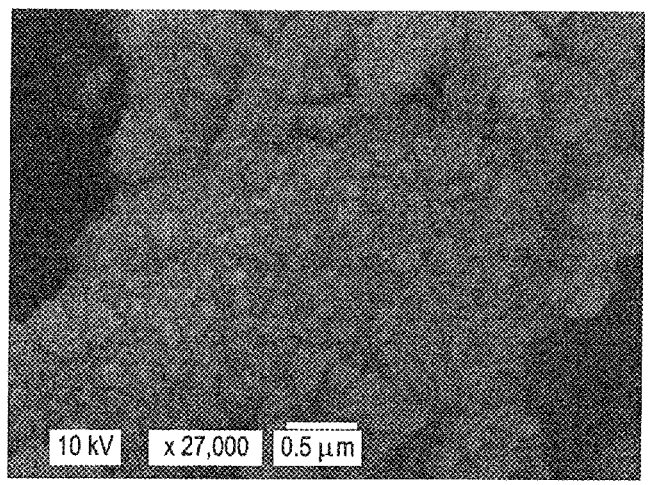
FIGS. 7A and 7B show the SEM of SiTH2-silver nanoparticles.
Figure 7B:
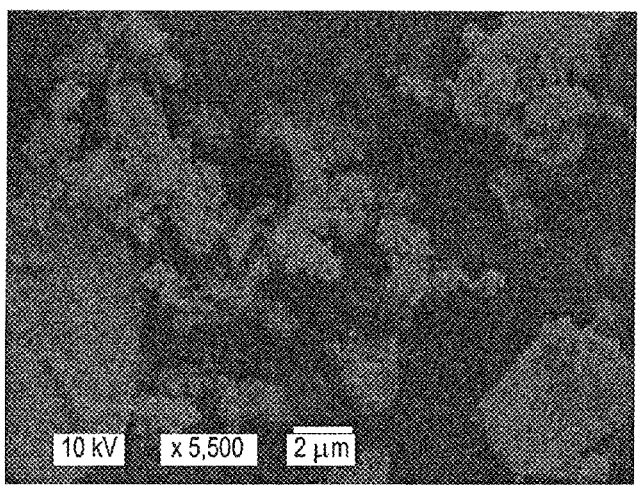
Figure 8:
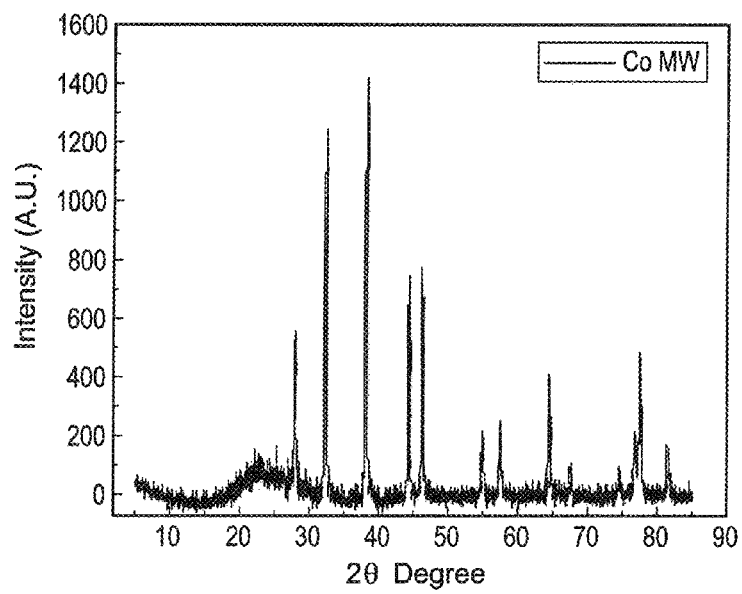
FIG. 8 shows the X-ray diffraction pattern of SiTH2-silver nanoparticle powder.

The elemental analysis of the AgNPs was performed using Energy-dispersive X-ray spectroscopy (EDX) on the transmission electron microscopy (TEM). EDX analysis confirmed the presence of the elementary silver signal of the prepared AgNPs, as shown in FIGS. 6 and 8, respectively. Signal peaks in the range of 2.5-4 keV were observed, which correspond to the binding energies of crystalline silver. Also, a strong signal peak near 0.2 keV corresponded to carbon in the ligand connected to AgNPs. On the other hand, several peaks for CuKα and CuKβ showed, which correspond to the TEM holding grid. These results were confirmed by previous reports that showed that AgNPs are crystalline in nature, with the same EDX results.

The XRD patterns (FIGS. 6 and 8) showed peaks at about 38.1θ, 44.09θ, 64.36 θ, 77.29θ, and 81.319 for both the prepared materials, which corresponded to 111, 200, 220, 311, 222, 400, 331, and 420 planes, respectively, to indicate a typical face-centered cubic structure of silver, as per the available literature (Joint Committee on Powder Diffraction Standards, JCPDS file No 04-0783).

Figure 9:
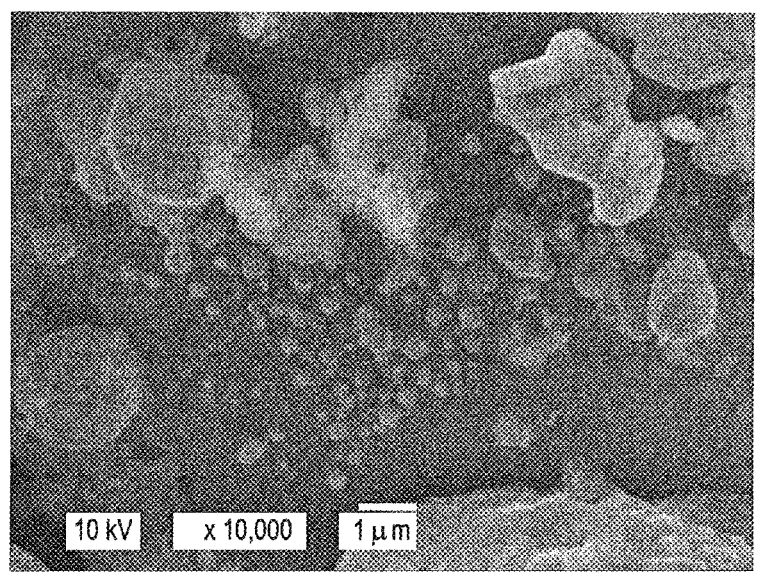
FIG. 9 shows the SEM of SiTH2-AgNPs powder.
Figure 10A:
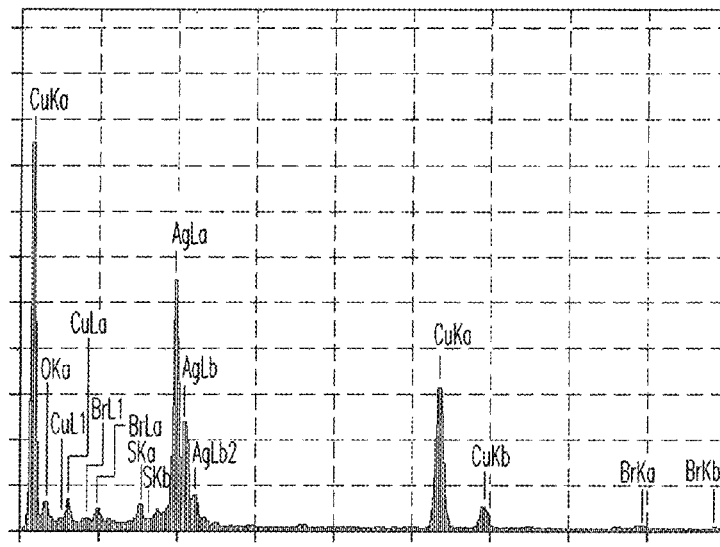
FIGS. 10A and 10B show the energy dispersive X-ray spectra of the prepared AgNPs from solution.
Figure 10B:
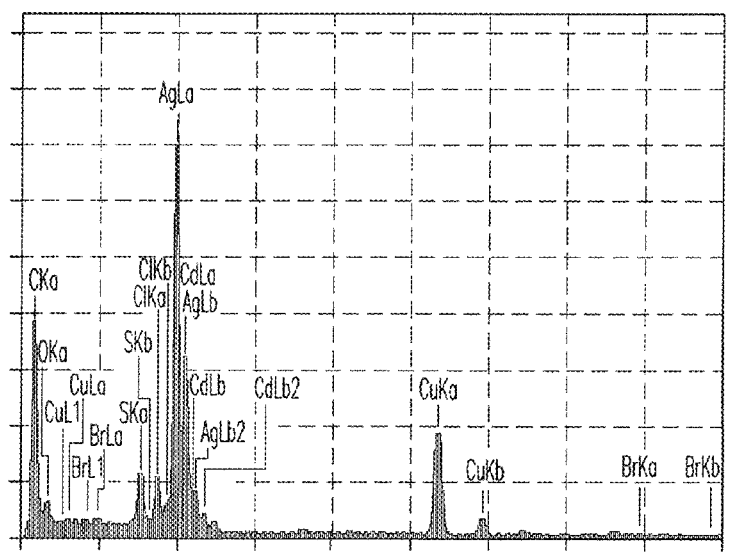
Figure 11:
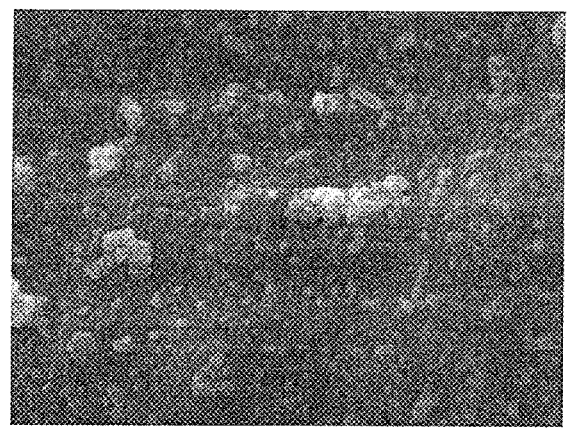
FIG. 11 shows the SEM for AgNPs powder form in solution.
Figure 12:
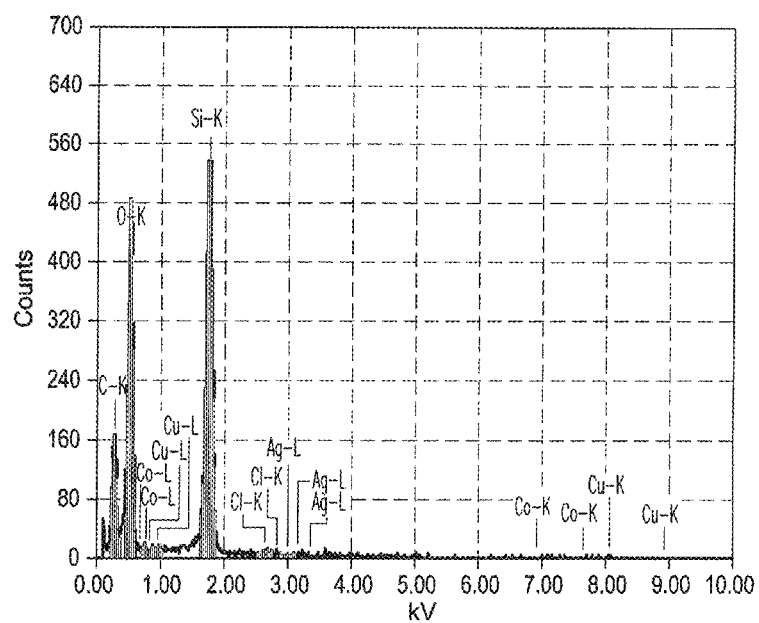
FIG. 12 is the Energy dispersive X-ray spectra of the prepared copper nanoparticles from SiTH2 in solution.
Figure 13:
FIG. 13 is the SEM of the copper nanoparticles prepared from the SiTH2 in solution.

A scanning electron microscope (JSM-5800 JEOL) was employed to study the structure of the prepared silver-ligand composite, as shown in FIGS. 7A, 7B, 9 and 11. The composite distribution of AgNPs over ligand surface is observed as shown in FIG. 9. FIGS. 10A and 10B show the energy dispersive X-ray spectra of the prepared AgNPs from solution. FIG. 11 shows the SEM for AgNPs powder form. Moreover, FIG. 12 is the energy dispersive X-ray spectra of the prepared copper nanoparticles from SiTH2 in solution. FIG. 13 is the SEM of the Copper nanoparticles prepared from the SiTH2 in solution.

Figure 14A:
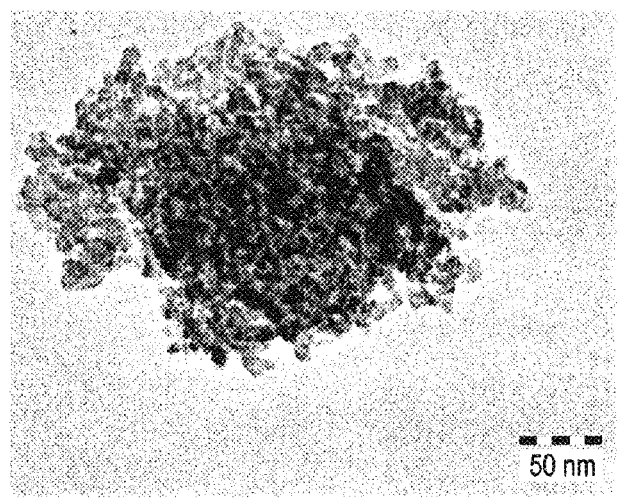
FIGS. 14A, 14B and 14C show transmission electron micrographs (TEMs) of the silver nanoparticles in solution.
Figure 14B:
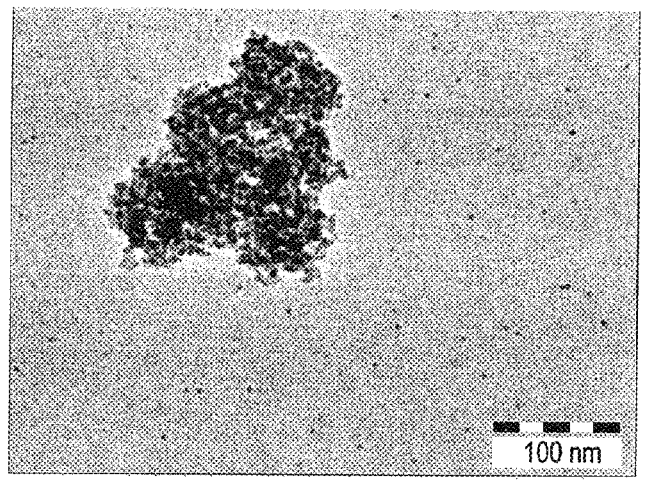
Figure 14C:
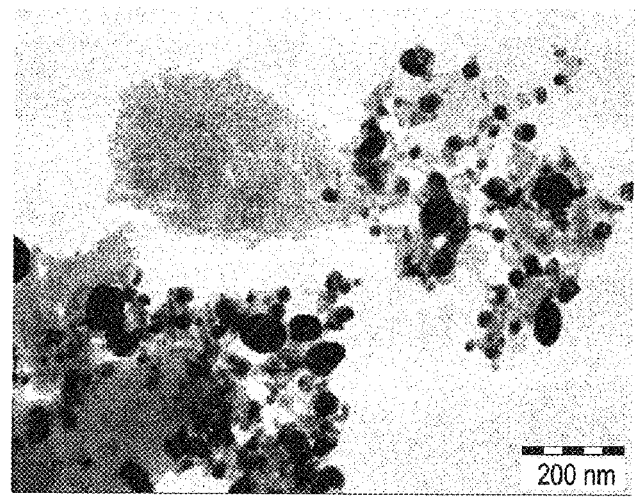

The TEM image of the synthesized silver nanoparticles (AgNPs) is represented in FIGS. 14A-14C. Analysis of TEM imaging shows that the prepared AgNPs are monodispersed spheres having a diameter in the range of 8-22 nm, as shown in Table 1.

TABLE 1

Particle Size Analysis of AgNPs

| Key or Sample | Crystallite Size (nm) | Lattice Strain |
|---|---|---|
| Ag Cockt solution | 6.859 | 0.0162 |
| Ag solution (filtered) | 22.740 | 0.0057 |
| Ag- Cockt solid heating | 60.46 | 0.0031 |
| Ag- Cockt solid MW | 7.909 | 0.014 |
| Activated solution | 22.29 | 0.0082 |

It is to be understood that the present invention is not limited to the embodiments described above, but encompasses any and all embodiments within the scope of the following claims.

We claim:

1. Functionalized silica for the synthesis of metal nanoparticles having the structural formula:

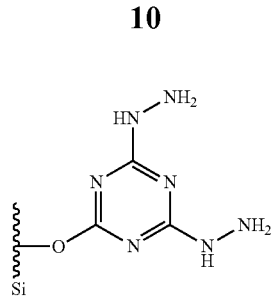

or the formula:

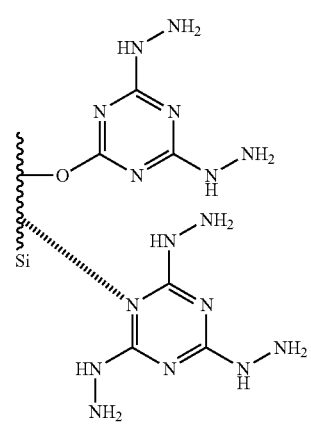

wherein Si is silica (SiO$_2$).

2. A method of preparing functionalized silica for the synthesis of metal nanoparticles of claim 1, comprising the steps of:
   combining silica gel and a triazine derivative in a first organic solvent to form a mixture;
   heating the mixture for about two hours;
   isolating a white solid by filtration;
   washing the solid with the first organic solvent;
   suspending the white solid in a second organic solvent to form a suspension;
   adding hydrazine hydrate to the suspension while stirring;
   heating the suspension for about 3 to 4 hours to form the silica surface functionalized by a hydrazino-triazine derivative; and
   isolating the silica surface functionalized by a hydrazino-triazine derivative by filtration.

3. The method of preparing functionalized silica for the synthesis of metal nanoparticles according to claim 2, further comprising the step of washing the solid product with the second organic solvent.

4. The method of preparing functionalized silica for the synthesis of metal nanoparticles according to claim 2, wherein the silica gel comprises activated silica gel, and wherein said activated silica gel is prepared by refluxing the silica gel with concentrated hydrochloric acid for about 24 hours; washing the silica gel with water until free of chloride; and drying the silica gel at about 100° C. for about 24 hours.

5. The method of preparing functionalized silica for the synthesis of metal nanoparticles according to claim 2, wherein the first organic solvent is dichloromethane and the second organic solvent is acetonitrile.

6. The method of preparing functionalized silica for the synthesis of metal nanoparticles according to claim 2, further comprising the step of heating the surface functionalized by a hydrazino-triazine derivative in an oven at 100° C. for about 12 hours.

7. A silica surface functionalized by a hydrazino-triazine derivative, the functionalized silica surface having the structural formula:

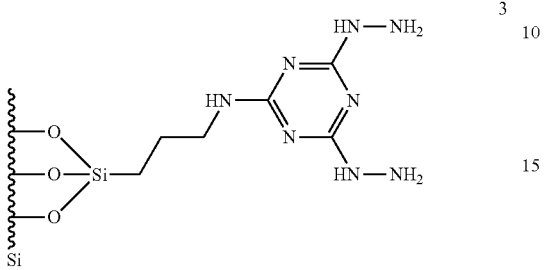

wherein Si is silica.

8. A method of preparing a silica surface functionalized by a hydrazino-triazine derivative of claim 7, comprising the steps of:
   reacting silica gel and 3-aminopropyltrimethoxysilane under reflux conditions for about eight hours in a first organic solvent to form silica-supported aminopropyltrimethoxysilane;
   isolating the silica-supported aminopropyltrimethoxysilane by filtration;
   washing the silica-supported aminopropyltrimethoxysilane with the first organic solvent;
   drying the silica-supported aminopropyltrimethoxysilane product at about 110° C.
   reacting the silica-supported aminopropyltrimethoxysilane with cyanuric chloride and diisopropylethylamine in a second organic solvent at room temperature under stirring for about 12 hours to form a silica-functionalized aminopropyltrimethoxysilane-diisopropylethylamine derivative;
   isolating the silica-functionalized aminopropyltrimethoxysilane-diisopropylethylamine derivative;
   washing the silica-functionalized aminopropyltrimethoxysilane-diisopropylethylamine derivative with a mixture of an organic solvent;
   drying the silica-functionalized aminopropyltrimethoxysilane-diisopropylethylamine derivative;
   reacting the silica-functionalized aminopropyltrimethoxysilane-diisopropylethylamine derivative with hydrazine hydrate under reflux conditions in ethanol for about 4 hours to form the silica surface functionalized by a hydrazino-triazine derivative; and
   isolating the silica surface-functionalized hydrazino-triazine derivative by filtration.

9. The method of method of preparing a silica surface functionalized by a hydrazino-triazine derivative according to claim 8, further comprising the step of washing the silica surface-functionalized hydrazino-triazine derivative with hot ethanol, ether and methanol.

10. The method of method of preparing a silica surface functionalized by a hydrazino-triazine derivative according to claim 8, wherein the silica gel is activated silica gel, said activated silica gel being prepared by refluxing the silica gel with concentrated hydrochloric acid for about 48 hours; washing with water until free of chloride and drying at about 100° C. for about 24 hours to obtain the activated silica gel.

11. The method of method of preparing a silica surface functionalized by a hydrazino-triazine derivative according to claim 8, wherein the first organic solvent is toluene and the second organic solvent is tetrahydrofuran.

12. The method of method of preparing a silica surface functionalized by a hydrazino-triazine derivative according to claim 8, wherein the mixture of organic solvent comprises tetrahydrofuran, dichloromethane and methanol.

* * * * *